(12) United States Patent
Nishikawa et al.

(10) Patent No.: US 9,540,638 B2
(45) Date of Patent: Jan. 10, 2017

(54) LIPID PARTICLE, NUCLEIC ACID TRANSFER CARRIER, COMPOUND FOR MANUFACTURING NUCLEIC ACID TRANSFER CARRIER, METHOD FOR MANUFACTURING LIPID PARTICLE, AND GENE TRANSFER METHOD

(71) Applicant: FUJIFILM Corporation, Tokyo (JP)

(72) Inventors: Naoyuki Nishikawa, Ashigarakami-gun (JP); Kyoko Senga, Ashigarakami-gun (JP); Yuuki Inoue, Ashigarakami-gun (JP); Yuko Igarashi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 163 days.

(21) Appl. No.: 14/314,873

(22) Filed: Jun. 25, 2014

(65) Prior Publication Data

US 2015/0004695 A1 Jan. 1, 2015

(30) Foreign Application Priority Data

Jun. 26, 2013 (JP) .................................. 2013-133620

(51) Int. Cl.
*C12N 15/11* (2006.01)
(52) U.S. Cl.
CPC ......... *C12N 15/111* (2013.01); *C12N 2310/14* (2013.01); *C12N 2310/141* (2013.01); *C12N 2320/32* (2013.01)
(58) Field of Classification Search
CPC .......................... C12N 15/111; C12N 2310/14
See application file for complete search history.

(56) References Cited

U.S. PATENT DOCUMENTS

| 4,788,182 | A | * | 11/1988 | Baschang | ................ | C07F 9/10 |
| | | | | | | 514/114 |
| 4,804,539 | A | * | 2/1989 | Guo | ....................... | A61K 9/127 |
| | | | | | | 264/4.3 |
| 5,958,901 | A | | 9/1999 | Dwyer et al. | | |
| 2009/0233366 | A1 | | 9/2009 | Kikuchi et al. | | |
| 2013/0017223 | A1 | | 1/2013 | Hope et al. | | |

FOREIGN PATENT DOCUMENTS

| JP | 11-507815 A | 7/1999 |
| JP | 2005-517739 A | 6/2005 |
| JP | 2011-21026 A | 2/2011 |
| WO | WO 2008/056623 A1 | 5/2008 |
| WO | WO 2010/026621 A1 | 3/2010 |
| WO | WO 2011/075656 A1 | 6/2011 |
| WO | WO 2012/000104 A1 | 1/2012 |

OTHER PUBLICATIONS

Mishra et al. Journal of Drug Delivery. 2011; 863734: 1-14).*
STIC Search—claim 5, Formula 1 (2016).*
Japanese Office Action for Japanese Application No. 2013-133620, dated Nov. 17, 2015, with an English translation.
Lv et al., "Toxicity of cationic lipids and cationic polymers in gene delivery", Journal of Controlled Release, vol. 114, 2006, pp. 100-109.
Wheeler et al., "Stabilized plasmid-lipid particles: construction and characterization", Gene Therapy, vol. 6, 1999, pp. 271-281.

* cited by examiner

*Primary Examiner* — Scott Long
(74) *Attorney, Agent, or Firm* — Birch, Stewart, Kolasch & Birch, LLP

(57) ABSTRACT

The present invention provides a lipid particle which has low cytotoxicity, can stably hold a nucleic acid molecule outside a cell (in blood), and can escape from an endosome and rapidly release the nucleic acid in the cytoplasm; a nucleic acid transfer carrier; a compound for manufacturing a nucleic acid transfer carrier; a method for manufacturing a lipid particle; and a gene transfer method. The lipid particle contains, as constituents, a phospholipid having one or more amino groups and one or more nitrogen-containing heterocyclic groups, a neutral lipid not containing a nitrogen-containing heterocyclic group, a sterol, and a nucleic acid.

16 Claims, No Drawings

LIPID PARTICLE, NUCLEIC ACID TRANSFER CARRIER, COMPOUND FOR MANUFACTURING NUCLEIC ACID TRANSFER CARRIER, METHOD FOR MANUFACTURING LIPID PARTICLE, AND GENE TRANSFER METHOD

CROSS-REFERENCE TO RELATED APPLICATIONS

The present application claims priority under 35 U.S.C. §119 to Japanese Patent Application No. 2013-133620, filed Jun. 26, 2013, all of which are hereby expressly incorporated by reference into the present application.

BACKGROUND OF THE INVENTION

1. Field of the Invention

The present invention relates to a lipid particle useful for transferring nucleic acids such as micro RNA (miRNA), asymmetrical interfering RNA (aiRNA), or small interfering RNA (siRNA) into a cell, a nucleic acid transfer carrier, a compound for manufacturing a nucleic acid transfer carrier, a method for manufacturing a lipid particle, and a gene transfer method.

2. Description of the Related Art

Nucleic acid medicines have a clear mechanism of action for diseases and cause fewer adverse effects, hence they are expected as next-generation pharmaceutical products. For example, nucleic acid medicines utilizing RNA interference (RNAi) can inhibit expression of a target gene by inducing degradation of messenger RNA (mRNA) of a target gene present in a cell. Consequentially, the medicines can relieve or treat symptoms of diseases caused by the abnormal expression of a specific gene or gene family. For the nucleic acid medicines utilizing RNA interference, for example, nucleic acids such as miRNA, aiRNA, or siRNA are used, and in order to cause these nucleic acids to carry out their function, the nucleic acids need to be transferred into a cell.

As a method for effectively transferring the nucleic acid into a cell, a carrier (vector) is generally used, and the carrier (vector) includes viral carriers and non-viral carriers. Many of the viral carriers have not been clarified in terms of pathogenicity, immunogenicity, and safety regarding cytotoxicity. Therefore, it is desirable to use non-viral carriers for clinical application. The nucleic acid is anionic, and accordingly, as the non-viral carriers, cationic carriers that can hold the nucleic acid by electrostatic interaction are used. As the cationic carriers, for example, a cationic liposome using cationic lipids having a specific structure, complexes using a cationic polymer, and the like are generally known. Examples of the cationic liposome include a liposome in which nucleic acids are bonded to the surface of a lipid bilayer membrane by electrostatic interaction, a lipoplex in which nucleic acids are bonded to the surface of a lipid bilayer membrane and interposed between the lipid bilayer membranes, and the like.

For example, Gene Therapy, Vol. 6, page 271, 1999 discloses a liposome consisting of a cationic lipid, 1,2-dioleoyl-3-sn-phosphatidylethanolamine (DOPE), and polyethylene glycol lipid. Moreover, WO2012/000104A1 discloses a lipid particle containing a cationic lipid in an amount of 50 mol % to 85 mol %, and WO2011/0756556A1 discloses a lipid particle using plural cationic lipids. Further, US2013/0017223A1 discloses a lipid particle consisting of a first cationic lipid, a second cationic lipid, a neutral lipid, and a polyethylene glycol lipid. In addition, various complexes using a cationic polymer are known (Journal of Controlled Release 114 (2006), 100-109).

As means for further improving the cationic carrier, for example, an amphoteric liposome obtained by combining cationic lipids with anionic lipids is disclosed in JP2011-21026A, and an amphoteric liposome consisting of an amphoteric-amphiphilic lipid is disclosed in JP2005-517739A.

SUMMARY OF THE INVENTION

Both the nucleic acid and cell membrane are anionic and electrically repel each other. Therefore, it is extremely difficult to directly transfer a nucleic acid such as DNA or RNA into a cell, and accordingly, there is a problem in that an effective therapeutic effect is not obtained. Further, the nucleic acid is unstable in blood, and this leads to a problem in that the nucleic acid is easily degraded when being directly administered into the body. As means for effectively transferring the nucleic acid into a cell, non-viral cationic carriers are used. However, generally, many of the carriers using cationic lipids are highly cytotoxic, and for example, Lipofectamine 2000 (registered trademark) as a commercially available gene transfer agent has extremely strong cytotoxicity. Likewise, complexes using a cationic polymer have a problem of cytotoxicity of the cationic polymer, hence a solution for the problem is desired to be found. As means for solving the problem of the cationic carriers, an amphoteric liposome which is obtained by combining cationic lipids with anionic lipids and an amphoteric liposome which consists of an amphoteric-amphiphilic lipid are under examination, but these have not been put to practical use.

An object of the present invention is to improve the performance of a nucleic acid carrier that is used in nucleic acid medicines or used as a gene transfer reagent. That is, an object of the present invention is to provide a lipid particle which has low cytotoxicity, can stably hold a nucleic acid molecule outside a cell (in blood), and can escape from an endosome and rapidly release the nucleic acid in the cytoplasm; a nucleic acid transfer carrier; a compound for manufacturing a nucleic acid transfer carrier; a method for manufacturing a lipid particle; and a gene transfer method.

The present inventors conducted thorough examination to achieve the above object. As a result, they found that by preparing a lipid particle which contains, as constituents, a phospholipid having one or more amino groups and one or more nitrogen-containing heterocyclic groups, neutral lipids not containing a nitrogen-containing heterocyclic group, a sterol, and a nucleic acid, a lipid particle resolving the above problem can be provided. The present invention has been completed based on the findings.

That is, according to the present invention, there is provided a lipid particle which contains, as constituents, a phospholipid having one or more amino groups and one or more nitrogen-containing heterocyclic groups, neutral lipids not containing a nitrogen-containing heterocyclic group, a sterol, and a nucleic acid.

The phospholipid having one or more amino groups and one or more nitrogen-containing heterocyclic groups is preferably a phospholipid having one or more amino groups and one or more imidazolyl groups.

The phospholipid having one or more amino groups and one or more nitrogen-containing heterocyclic groups preferably has a structure in which a carboxyl group of histidine is bonded to an amino group of phospholipid having the amino group.

The phospholipid having one or more amino groups and one or more nitrogen-containing heterocyclic groups is preferably a lipid represented by the following Formula (I) or a salt thereof.

Formula (I)

[Chem. 1]

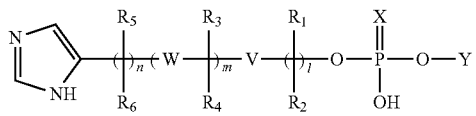

(In Formula (I), X represents an oxygen atom or a sulfur atom; Y represents a hydrophobic group; each of W and V independently represents a single bond, —O—, —NH—, —CO—, or a linking group as a combination of these; each of $R_1$ and $R_2$ independently represents a hydrogen atom or an alkoxycarbonyl group having 1 to 4 carbon atoms; each of $R_3$ and $R_4$ independently represents a hydrogen atom, an alkyl group having 1 to 4 carbon atoms, a hydroxy alkyl group having 1 to 4 carbon atoms, an alkoxycarbonyl group having 1 to 4 carbon atoms, an aminoalkyl group having 1 to 4 carbon atoms, a guanidinoalkyl group having 1 to 4 carbon atoms, or an imidazolylalkyl group having 4 to 7 carbon atoms; each of $R_5$ and $R_6$ independently represents a hydrogen atom, an amino group, or an alkoxycarbonyl group having 1 to 4 carbon atoms; when n is 1, at least one of $R_5$ and $R_6$ represents an amino group, when n is an integer from 2 to 4, at least one of the plural $R_5$s and plural $R_6$s contained in Formula (I) represents an amino group; l represents an integer from 2 to 4; m represents an integer from 0 to 4, and n represents an integer from 1 to 4.)

The phospholipid having one or more amino groups and one or more nitrogen-containing heterocyclic groups is preferably a lipid represented by the following Formula (II) or Formula (III) or a salt thereof.

Formula (II)

[Chem. 2]

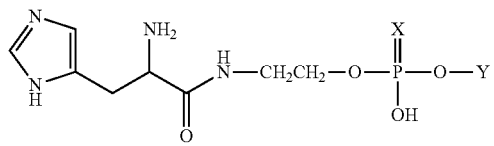

(In Formula (II), X represents an oxygen atom or a sulfur atom, and Y represents a hydrophobic group.)

Formula (III)

[Chem. 3]

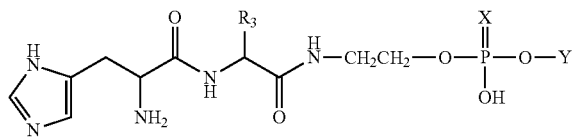

(In Formula (III), $R_3$ represents a hydroxyalkyl group having 1 to 4 carbon atoms or an imidazolylalkyl group having 4 to 7 carbon atoms; X represents an oxygen atom or a sulfur atom, and Y represents a hydrophobic group.)

The neutral lipid not containing a nitrogen-containing heterocyclic group is preferably phosphatidylethanol amine.

The neutral lipid not containing a nitrogen-containing heterocyclic group is preferably a phosphatidylethanolamine having a phase transition point of equal to or lower than 0° C.

The sterol is preferably cholesterol.

The lipid particle of the present invention preferably further contains polyethylene glycol-containing lipid.

The lipid particle of the present invention preferably further contains lipid having an antibody or a ligand.

The lipid having an antibody or a ligand is preferably a lipid having a polyethylene glycol chain.

The nucleic acid is preferably miRNA, aiRNA, or siRNA.

The lipid particle of the present invention is preferably non-liposomal.

According to the present invention, there is also provided a nucleic acid transfer carrier containing phospholipid having one or more amino groups and one or more nitrogen-containing heterocyclic groups, a neutral lipid not containing a nitrogen-containing heterocyclic group, and a sterol.

The nucleic acid transfer carrier of the present invention is preferably used as a gene transfer reagent or as a nucleic acid transfer carrier in a nucleic acid medicine.

According to the present invention, there is also provided a compound for manufacturing a nucleic acid transfer carrier which contains, as constituents, a phospholipid having one or more amino groups and one or more nitrogen-containing heterocyclic groups, a neutral lipid not containing a nitrogen-containing heterocyclic group, a sterol, and an organic solvent.

According to the present invention, there is also provided a method for manufacturing the lipid particle of the present invention that includes a step of manufacturing a dispersion consisting of a nucleic acid and a lipid by mixing an organic solvent solution, which contains phospholipid having one or more amino groups and one or more nitrogen-containing heterocyclic groups, a neutral lipid not containing a nitrogen-containing heterocyclic group, and a sterol, with a solution containing a nucleic acid, and a step of removing the organic solvent from the dispersion.

According to the present invention, there is also provided an intracellular gene transfer method including a step of transferring the lipid particle of the present invention into a cell in vitro.

The lipid particle of the present invention has low cytotoxicity. Moreover, according to the lipid particle of the present invention, it is possible to make a nucleic acid effectively perform its original function in a target cell.

DESCRIPTION OF THE PREFERRED EMBODIMENTS

Hereinafter, the present invention will be described in detail.

In the present specification, if there are plural kinds of substances corresponding to the respective components in the lipid particle, unless otherwise specified, the amount of the respective components with respect to a total amount of lipid (including a sterol) constituting the lipid particle refers to a total amount of the plural substances present in the lipid particle.

(1) Components of Lipid Particle

The lipid particle of the present invention contains, as constituents, a phospholipid having one or more amino groups and one or more nitrogen-containing heterocyclic groups, a neutral lipid not containing a nitrogen-containing heterocyclic group, a sterol, and a nucleic acid.

(a) Phospholipid Having One or More Amino Groups and One or More Nitrogen-Containing Heterocyclic Groups In the phospholipid that is used in the present invention and has one or more amino groups and one or more nitrogen-containing heterocyclic groups, the nitrogen-containing heterocyclic group refers to a heterocyclic group as a 5-membered ring, a 6-membered ring, or a condensed ring thereof having at least one nitrogen atom. Specifically, examples thereof include an imidazolyl group, a pyrazolyl group, a triazolyl group, a benzimidazolyl group, a pyridyl group, a pyrimidino group, a quinolino group, an isoquinolino group, and the like. Among these, an imidazolyl group, a pyrazolyl group, a benzimidazolyl group, and a pyridyl group are preferable, and an imidazolyl group is particularly preferable. The heterocyclic group may have substituents. The substituents of the heterocyclic group are not particularly limited, and examples thereof include a halogen atom, an alkyl group having 1 to 6 carbon atoms, a cycloalkyl group having 3 to 8 carbon atoms, an alkoxy group having 1 to 6 carbon atoms, and the like.

The phospholipid having one or more amino groups and one or more nitrogen-containing heterocyclic groups preferably has a structure in which a carboxyl group of histidine is bonded to an amino group of phospholipid having the amino group.

Examples of preferable embodiments of the phospholipid having one or more amino groups and one or more nitrogen-containing heterocyclic groups include lipids represented by the following Formula (I) or a salt thereof.

[Chem. 4]

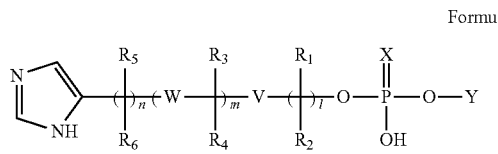

Formula (I)

In Formula (I), X represents an oxygen atom or a sulfur atom and preferably is an oxygen atom. Y represents a general hydrophobic group forming phospholipid. Specifically, examples thereof include an alkyl group having 8 to 24 carbon atoms, an acyl group having 8 to 22 carbon atoms, a 1,2-dialkyloxypropyl group having 16 to 54 carbon atoms, a 1,3-dialkyloxypropyl group having 16 to 54 carbon atoms, a 1,2-diacyloxypropyl group having 16 to 54 carbon atoms, a 1,3-diacyloxypropyl group having 16 to 54 carbon atoms, and the like. Among these, a 1,2-diacyloxypropyl group, a 1,3-diacyloxypropyl group having 16 to 54 carbon atoms, and the like are preferable. More specifically, particularly preferable examples thereof include a 1,2-ditetradecyloxypropyl group, 1,2-dihexadecyloxypropyl group, a 1,2-dioctadecyloxypropyl group, 1,2-dimyristoyloxypropyl group, a 1,2-dipalmitoyloxypropyl group, a 1,2-distearoyloxypropyl group, a 1,2-dioleoyloxypropyl group, a 1,2-dilinoleoyloxypropyl group, a 1,2-diphytanoyloxypropyl group, a 1-palmitoyloxy-2-dioleoyloxypropyl group, and the like.

In Formula (I), each of W and V independently represents a single bond, —O—, —NH—, —CO—, or a linking group as a combination of these. Preferable examples thereof include a single bond, a —O— group, a —NH— group, a —CO— group, a —COO— group, a —OCO— group, a —CO—NH— group, a —NH—CO— group, a —NH—CO—NH— group, and the like. Moreover, particularly preferable examples thereof include a single bond, a —COO— group, a —OCO— group, a —CO—NH— group, and a —NH—CO— group. Each of $R_1$ and $R_2$ independently represents a hydrogen atom or an alkoxycarbonyl group having 1 to 4 carbon atoms, and preferably is a hydrogen atom. Each of $R_3$ and $R_4$ independently represents a hydrogen atom, an alkyl group having 1 to 4 carbon atoms, a hydroxyalkyl group having 1 to 4 carbon atoms, an alkoxycarbonyl group having 1 to 4 carbon atoms, an aminoalkyl group having 1 to 4 carbon atoms, a guanidinoalkyl group having 1 to 4 carbon atoms, or an imidazolylalkyl group having 4 to 7 carbon atoms. Among these, a hydrogen atom, a hydroxyalkyl group having 1 to 4 carbon atoms, and an imidazolylalkyl group having 4 to 7 carbon atoms are preferable. Each of $R_5$ and $R_6$ independently represents a hydrogen atom, an amino group, or an alkoxycarbonyl group having 1 to 4 carbon atoms. When n is 1, at least one of the $R_5$ and $R_6$ represents an amino group. When n is an integer from 2 to 4, at least one of the plural $R_5$s and plural $R_6$s contained in Formula (I) represents an amino group. l represents an integer from 2 to 4 and preferably is 2. m represents an integer from 0 to 4, and is preferably 0 or an integer from 2 to 4. n represents an integer from 1 to 4 and is preferably an integer from 2 to 3.

The lipid represented by Formula (I) or a salt thereof is preferably a lipid represented by the following Formula (II) or Formula (III) or a salt thereof.

Formula (II)

[Chem. 5]

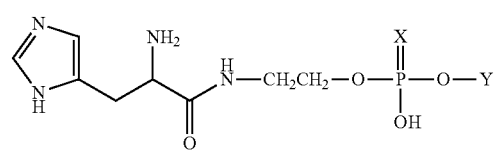

(In Formula (II), X represents an oxygen atom or a sulfur atom, and Y represents a hydrophobic group.)

Formula (III)

[Chem. 6]

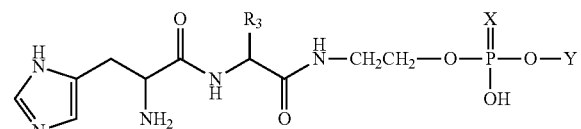

(In Formula (III), $R_3$ represents a hydroxyalkyl group having 1 to 4 carbon atoms or an imidazolylalkyl group having 4 to 7 carbon atoms; X represents an oxygen atom or a sulfur atom; and Y represents a hydrophobic group.)

The compound of Formula (II) can be synthesized by a synthesis method that is disclosed in JP1986-43193A (JP-S61-43193A) together with a drug for preventing and treating viral infections.

The compound of Formula (II) can also be synthesized by the following Scheme 1. Histidine, which is obtained by protecting an amino group and an imidazolyl group with an appropriate amino protecting group, or an active ester of histidine is condensed with phophatidylethanolamine, and then the resultant is subjected to deprotection, whereby the compound can be synthesized. As the amino protecting group, a general amino protecting group such as a Boc group or a Fmoc group can be used. As the active ester of histidine protected with an amino protecting group, for example, an ester of nitrophenol, N-hydroxysuccinimide, pentafluorophenol, and the like can be used.

For the condensation of histidine protected with an amino protecting group and phosphatidylethanolamine, it is possible to use general methods such as a method of using N,N'-dicyclohexylcarbodiimide (DCC), diisopropylcarbodiimide (DIPCDI), carbodiimide, 1-ethyl-3-(3-dimethylaminopropyl)carbodiimide (EDC or WSC), or the like as a condensation agent. At this time, in order to prevent epimerization, an additive such as 1-hydroxybenzotriazole (HOBt) or 3,4-dihydro-3-hydroxy-4-oxo-1,2,3-benzotriazine (HOOBt) may be added. The reaction can be performed in an organic solvent, an aqueous solvent, or a mixed solvent thereof. If necessary, an organic base such as triethylamine or diisopropylethylamine or an inorganic base such as sodium hydrogen carbonate can be used.

The active ester of histidine protected with an amino protecting group can be condensed by a general method. For example, the active ester of histidine protected with an amino protecting group and phosphatidylethanolamine may be condensed in an organic solvent, an aqueous solvent, or a mixed solvent thereof. At this time, if necessary, an organic base such as triethylamine or diisopropylethylamine or an inorganic base such as sodium hydrogen carbonate can be used.

By deprotecting the protected compound of Formula (II) obtained by the above method, a compound of the compound (II) can be obtained as intended. For the deprotection step, a method appropriate for the used amino protecting group is employed. For example, when a Boc group is used as the amino protecting group, deprotection can be performed using a hydrochloric acid solution of dioxane or trifluoroacetic acid.

Scheme I

[Chem. 7]

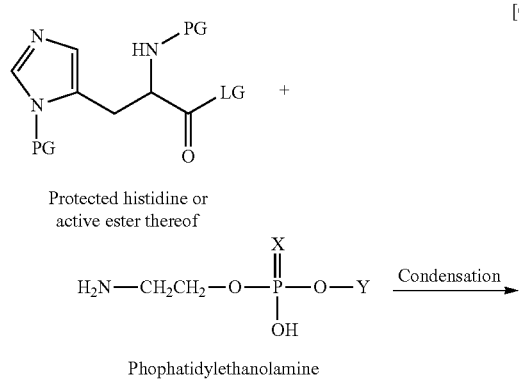

Protected histidine or active ester thereof

Phophatidylethanolamine

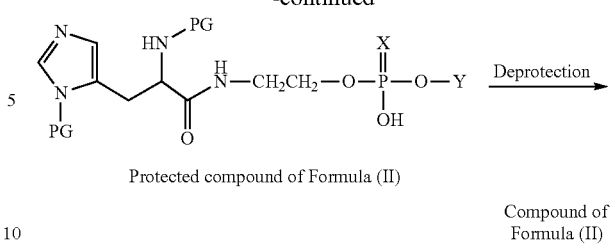

Protected compound of Formula (II)

Deprotection

Compound of Formula (II)

In the Formula, PG represents a protecting group, and LG represents a hydroxyl group or a leaving group constituting the active ester. X and Y have the same definition as described above.

Likewise, the compound of Formula (III) can be synthesized by the following Scheme 2. A step of condensing a protected histidine derivative with phosphatidylethanolamine and a step of deprotecting the protected compound of Formula (III) are performed in the same manner as described above in regard to Formula (II).

Scheme 2

[Chem. 8]

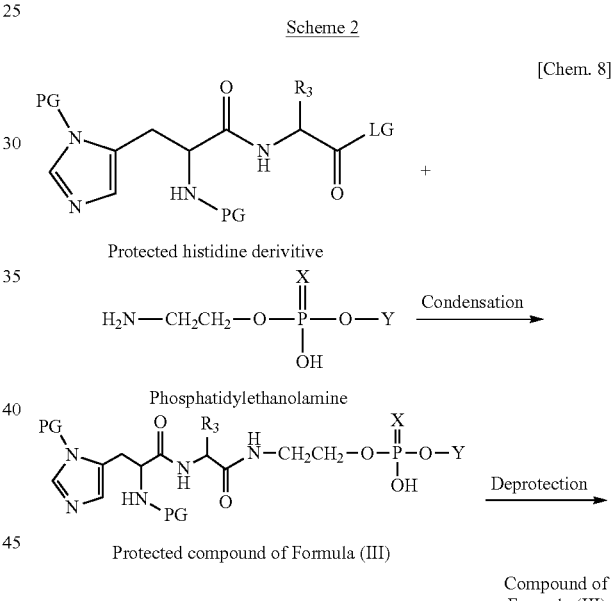

Protected histidine derivitive

Phosphatidylethanolamine

Condensation

Protected compound of Formula (III)

Deprotection

Compound of Formula (III)

In the formula, PG, LG, X, and Y have the same definition as described above.

When the phospholipid having one or more amino groups and one or more nitrogen-containing heterocyclic groups forms a salt, it is preferable for the phospholipid to form a medically acceptable salt such as an alkali metal salt, an alkaline earth metal salt, hydrochloride, acetate, sulfate, oxalate, or a succinate.

An optically active center of the phospholipid having one or more amino groups and one or more nitrogen-containing heterocyclic groups may be any of an S isomer, an R isomer, or an racemic mixture.

Particularly preferable examples of the phospholipid having one or more amino groups and one or more nitrogen-containing heterocyclic groups will be described below in detail. However, the present invention is not limited thereto.

Compound 1-1
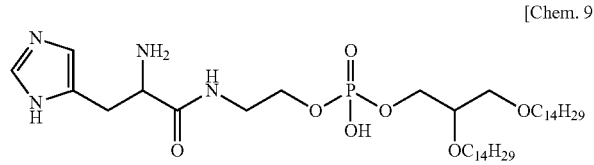
Compound 1-2
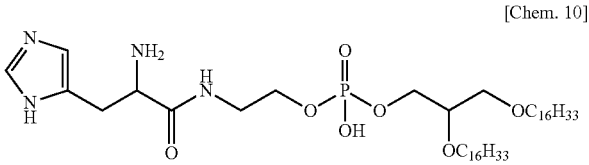
Compound 1-3
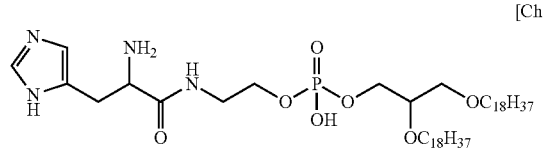
Compound 1-4
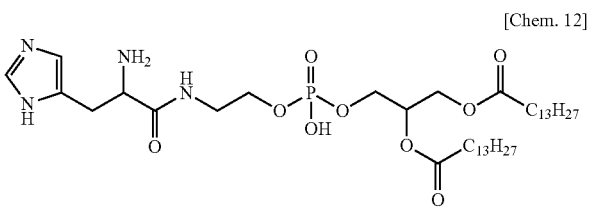
Compound 1-5
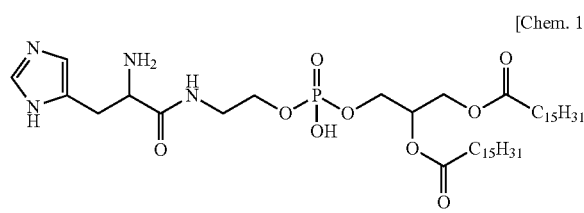
Compound 1-6
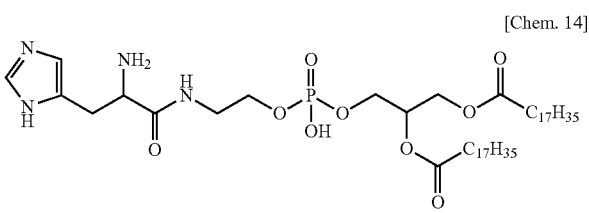
Compound 1-7
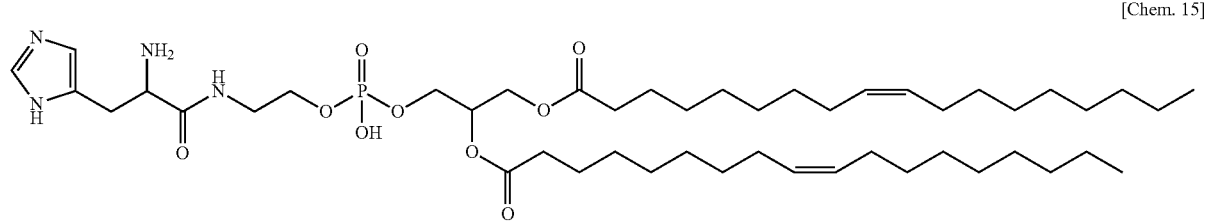
Compound 1-8
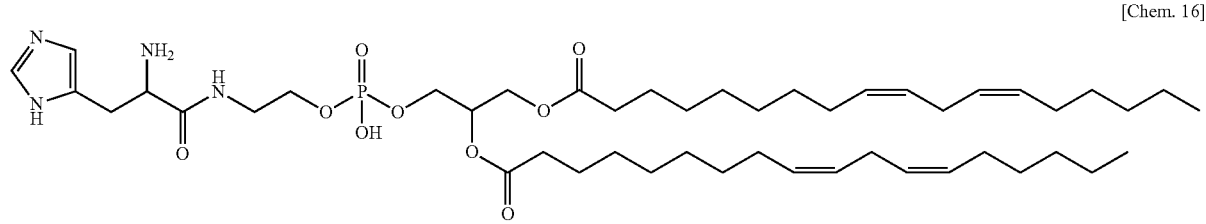
Compound 1-9
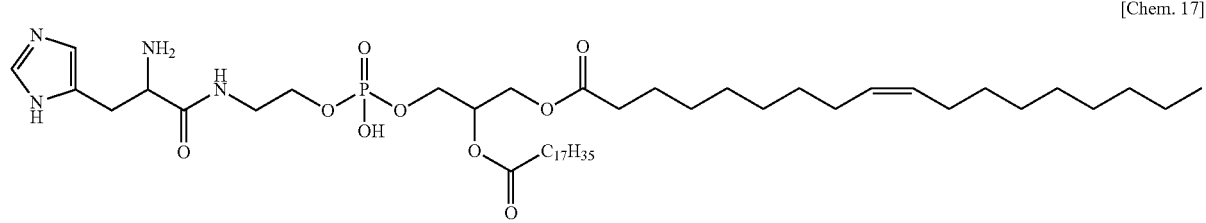

Compound 1-10

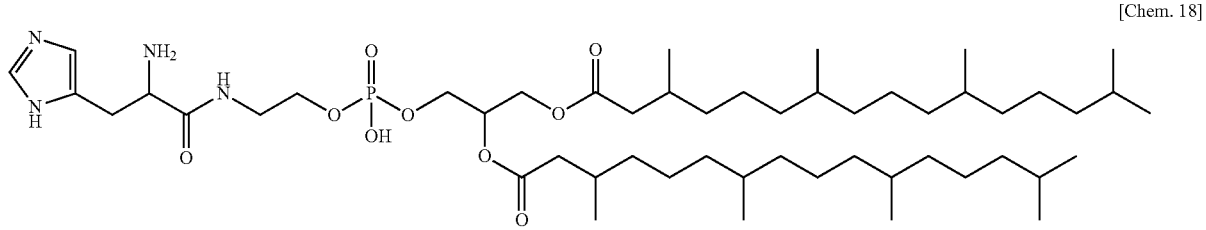

Compound 3-1

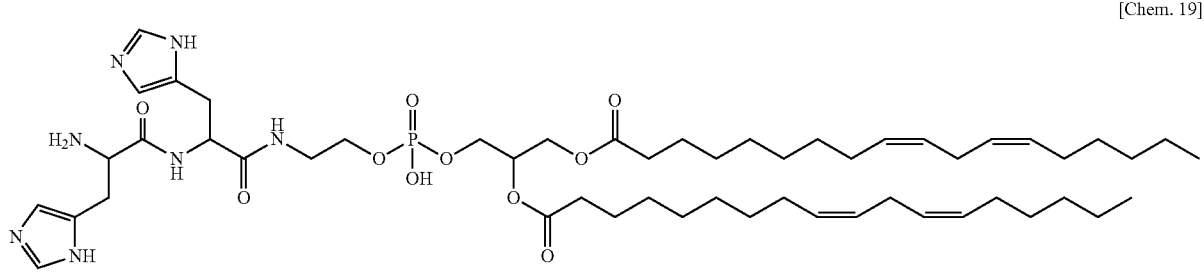

Compound 3-2

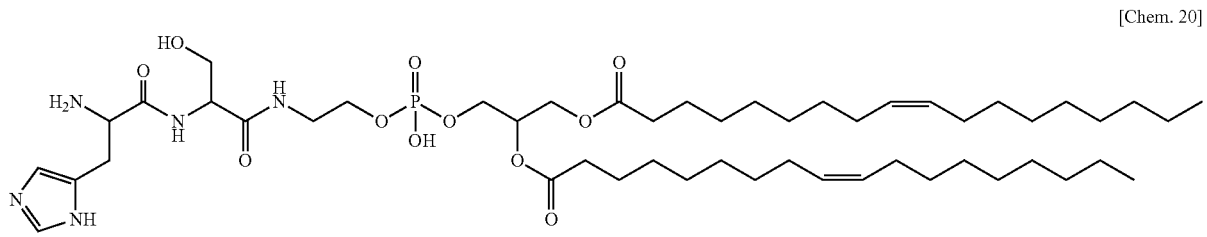

In the present invention, the amount of the phospholipid having one or more amino groups and one or more nitrogen-containing heterocyclic groups is preferably from 1 mol % to 60 mol %, more preferably from 3 mol % to 50 mol %, and even more preferably from 5 mol % to 40 mol % of a total amount of lipid (including a sterol) constituting the lipid particle.

(b) Neutral Lipid not Containing Nitrogen-Containing Heterocyclic Group

The neutral lipid, which is used in the present invention and does not contain a nitrogen-containing heterocyclic group, is not particularly limited, and examples thereof include a phosphatidylcholine, a phosphatidylethanolamine, a sphingomyelin, and a ceramide. As the neutral lipid not containing a nitrogen-containing heterocyclic group, a phosphatidylethanolamine is preferable, and particularly, a phosphatidylethanolamine having a phase transition point of equal to or lower than 0° C. is preferable. The neutral lipid not containing a nitrogen-containing heterocyclic group may be used singly or used in the form of a combination of plural different "neutral lipids not containing a nitrogen-containing heterocyclic group". When the combination of plural different "neutral lipids not containing a nitrogen-containing heterocyclic group" is used, at least one of the "neutral lipids not containing a nitrogen-containing heterocyclic group" is preferably a phosphatidylethanolamine and particularly preferably a phosphatidylethanolamine having a phase transition point of equal to or lower than 0° C. The phase transition point can be measured by a general method. For example, it can be measured using a differential scanning calorimeter (DSC).

The phosphatidylcholine is not particularly limited, and examples thereof include soybean lecithin (SPC), hydrogenated soybean lecithin (HSPC), egg yolk lecithin (EPC), hydrogenated egg yolk lecithin (HEPC), dimyristoylphosphatidylcholine (DMPC), dipalmitoylphosphatidylcholine (DPPC), distearoylphosphatidylcholine (DSPC), dioleoylphosphatidylcholine (DOPC), dilinoleoylphosphatidylcholine (DLoPC), 1-palmitoyl-2-oleoylphosphatidylcholine (POPC), and the like.

The phosphatidylethanolamine is not particularly limited, and examples thereof include dimyristoyl phosphatidylethanolamine (DMPE), dipalmitoyl phosphatidylethanolamine (DPPE), distearoyl phosphatidylethanolamine (DSPE), dioleoyl phosphatidylethanolamine (DOPE), dilinoleoyl phosphatidylethanolamine (DLoPE), diphytanoyl phosphatidylethanolamine (D(Phy)PE), 1-palmitoyl-2-oleoyl phosphatidylethanolamine (POPE), ditetradecyl phosphatidylethanolamine, dihexadecyl phosphatidylethanolamine, dioctadecyl phosphatidylethanolamine, diphytanyl phosphatidylethanolamine, and the like. Among these, dioleoyl phosphatidylethanolamine (DOPE), dilinoleoyl phosphatidylethanolamine (DLoPE), and diphytanoyl phosphatidylethanolamine (D(Phy)PE) are particularly preferable.

The sphingomyelin is not particularly limited, and examples thereof include egg yolk-derived sphingomyelin, milk-derived sphingomyelin, and the like.

The ceramide is not particularly limited, and examples thereof include egg yolk-derived ceramide, milk-derived ceramide, and the like.

In the present invention, the amount of the neutral lipid not containing a nitrogen-containing heterocyclic group is preferably from 5 mol % to 70 mol %, more preferably from 10 mol % to 60 mol %, and even more preferably from 20 mol % to 50 mol % of a total amount of lipid (including a sterol) constituting the lipid particle.

(c) Sterol

The sterol used in the present invention is not particularly limited, and examples thereof include cholesterol, phytosterol (sitosterol, stigmasterol, fucosterol, spinasterol, brassicasterol, or the like), ergosterol, cholestanone, cholestenone, coprostanol, cholesteryl-2'-hydroxyethyl ether, cholesteryl-4'-hydroxybutyl ether, and the like. Among these, cholesterol is particularly preferable.

In the present invention, the amount of the sterol is preferably from 5 mol % to 70 mol %, more preferably from 10 mol % to 60 mol %, and even more preferably from 20 mol % to 50 mol % of a total amount of lipid (including a sterol) constituting the lipid particle.

(d) Nucleic Acid

The nucleic acid used in the present invention includes known nucleic acids in any form. Specific examples of the nucleic acid include single-stranded DNA or RNA, double-stranded DNA or RNA, a DNA-RNA hybrid, and the like. Examples of the double-stranded DNA include structural genes, genes having a control region and a termination region, viral DNA, plasmid DNA, and the like. Examples of the double-stranded RNA include siRNA, aiRNA, miRNA, and the like. Examples of the single-stranded nucleic acid include antisense oligonucleotide, ribozyme, and the like. Among these, it is preferable to use miRNA, aiRNA, or siRNA as the nucleic acid.

The nucleic acid used in the present invention may be a non-natural nucleic acid. Examples of the non-natural nucleic acid include non-natural nucleic acids having at least one 2'OMe purine or pyrimidine nucleotide such as 2'OMe-guanosine, 2'OMe-uridine, 2'OMe-adenosine, and/or 2'OMe-cytosine nucleotide. Moreover, preferable examples thereof also include non-natural nucleic acids (BNA and LNA) and the like having two cyclic structures that are formed when oxygen atoms in the position 2' of the nucleic acid are crosslinked with carbon atoms at the position 4' via methylene. In the present invention, various non-natural nucleic acids can be used, and the present invention is not limited to the above nucleic acids. Further, the nucleic acid used in the present invention may have an overhang structure disclosed in, for example, Elbashir et al., Genes Dev., 15:188 (2001) or Nykanen et al., Cell, 107:309 (2001).

The amount of the used nucleic acid with respect to a total amount of lipid that is expressed in terms of mass (mass of nucleic acid/total mass of lipid) is not particularly limited, and is preferably 0.001 to 2 and more preferably 0.01 to 1.

(e) Polyethylene Glycol-Containing Lipid

In the present invention, as one of the preferable embodiments, polyethylene glycol-containing lipid is concurrently used so as to inhibit aggregation of particles and to improve stability or retentivity of the carrier in blood. However, in the present invention, the use of polyethylene glycol (hereinafter, abbreviated to PEG in some cases)-containing lipid is not essential. Examples of the PEG-containing lipid include PEG-modified phosphoethanolamine, PEG derivatives of diacylglycerol, PEG derivatives of dialkylglycerol, PEG derivatives of cholesterol, PEG derivatives of ceramide, and the like. The molecular weight of a PEG chain is preferably 500 to 5,000 and particularly preferably 500 to 3,000. The PEG chain may be branched or may have a substituent such as a hydroxymethyl group.

When the PEG-containing lipid is used in the present invention, the amount of the PEG-containing lipid is preferably from 0.01 mol % to 10 mol %, more preferably from 0.05 mol % to 7 mol %, and even more preferably from 0.1 mol % to 5 mol % of a total amount of lipid (including a sterol) constituting the lipid particle.

(f) Lipid Having Antibody or Ligand

In the present invention, as an example of preferable embodiments, a lipid having an antibody or a ligand is concurrently used if necessary so as to improve targeting performance or cellular uptake performance of the nucleic acid carrier. However, in the present invention, the use of a lipid having an antibody or a ligand is not essential. For example, it is preferable for the lipid having an antibody or a ligand to be a lipid having a PEG chain. Examples of such lipid include a lipid linked with an antibody, a lipid linked with a cell membrane-permeable peptide, a lipid linked with an integrin ligand, a lipid linked with a transferrin, a lipid linked with folic acid, a lipid linked with a sugar ligand, and the like.

Specifically, it is possible to use the following lipids having a known antibody or ligand. Specific examples of the lipid linked with a cell membrane-permeable peptide include STR-R8 (Compound 4-1) disclosed in Journal of Controlled Release 143 (2010), 311-317. Specific examples of the lipid linked with an integrin ligand include RGD-related peptide-linked lipids (Compound 4-3 and Compound 4-4) disclosed in Life Sciences, 58 (1996), 2263-2270, RGDfK-linked PEG lipid (Compound 4-5) disclosed in Journal of Controlled Release 153 (2011), 141-148; RGDfS-linked PEG lipid (Compound 4-6) disclosed in Journal of Controlled Release 160 (2012), 177-181; and the like. Specific examples of the lipid linked with folic acid include folic acid-linked PEG lipid (Compound 4-7) disclosed in Bioconjugate Chemistry, vol. 10, No. 2, pp 289-298, 1999. Specific examples of the lipid linked with a sugar ligand include lipid (Compound 4-8) disclosed in Journal of Pharmaceutical Sciences, Vol. 94, 2266-2275 (2005), and the like.

In the present invention, the amount of the lipid having an antibody or a ligand is preferably from 0.01 mol % to 10 mol %, more preferably from 0.05 mol % to 7 mol %, and even more preferably from 0.1 mol % to 5 mol % of a total amount of lipid (including a sterol) constituting the lipid particle.

Compound 4-1
C17H35CO-Arg-Arg-Arg-Arg-Arg-Arg-Arg-Arg   (STR-R8)
Compound 4-2
[Chem. 21]
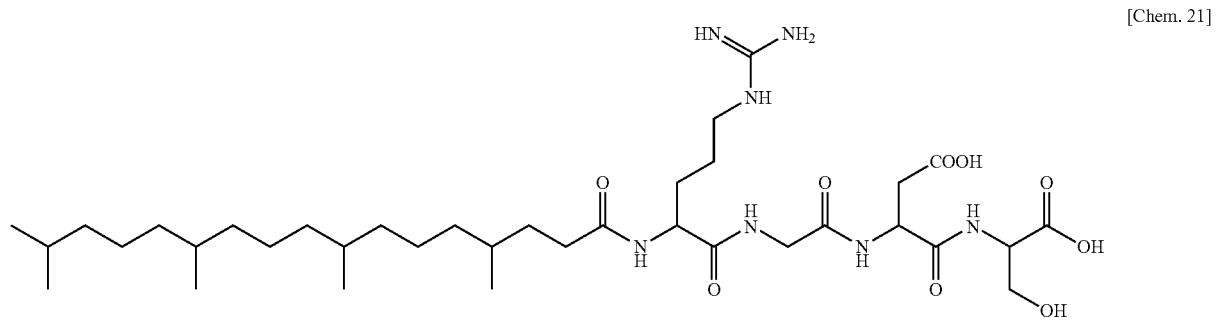
Compound 4-3
[Chem. 22]
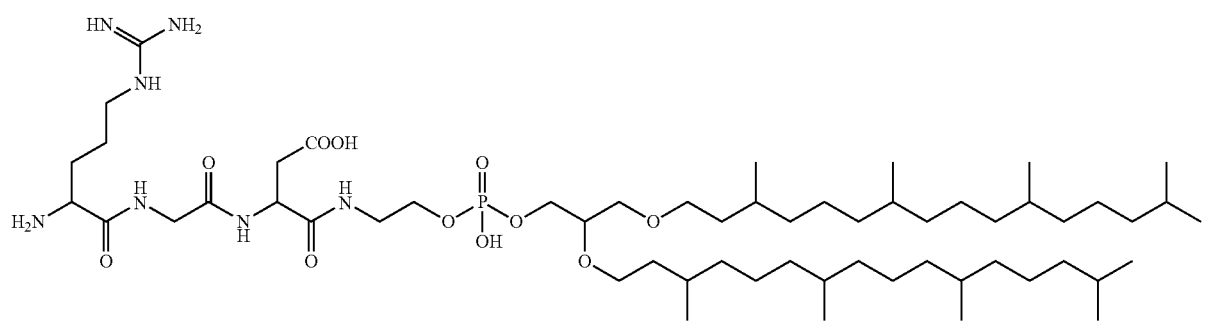
Compound 4-4
[Chem. 23]
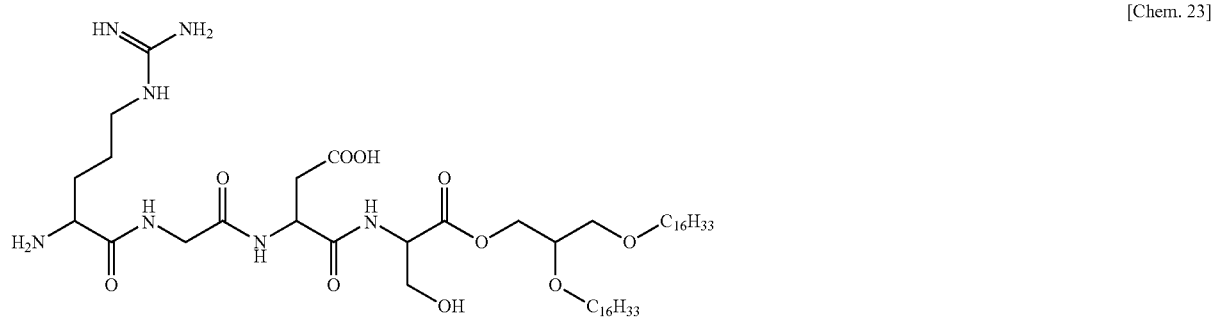
Compound 4-5
[Chem. 24]
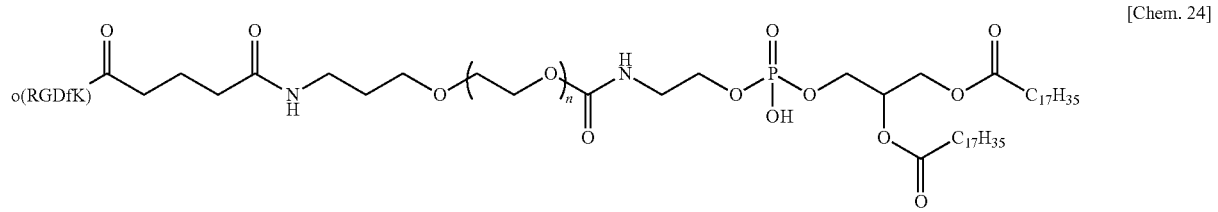
Compound 4-6
[Chem. 25]
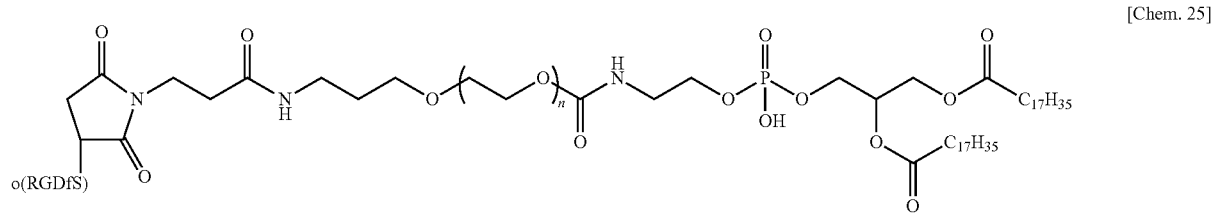

Compound 4-7

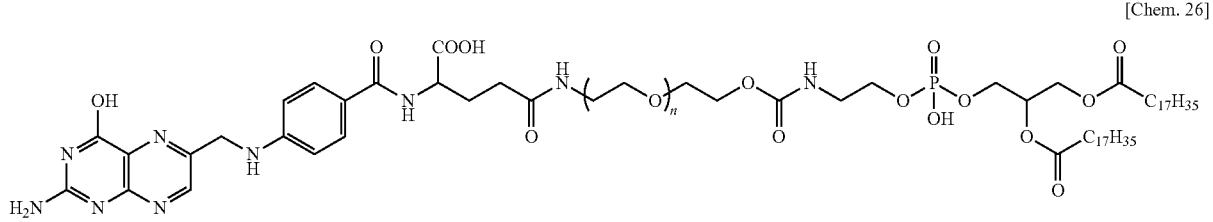

[Chem. 26]

Compound 4-8

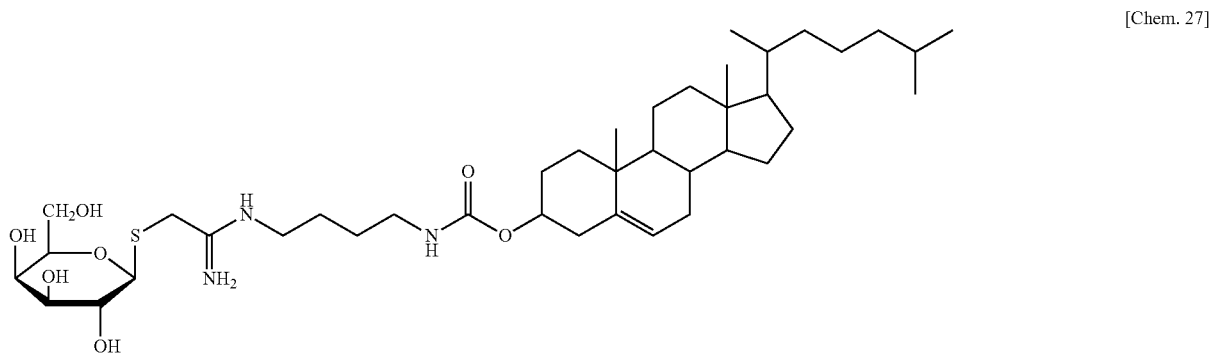

[Chem. 27]

(g) Other Constituents

If necessary, constituents other than the constituents disclosed in the above sections (a) to (f) may be added to the lipid particle of the present invention. Examples of such constituents include a glycerol ester and a sugar ester. However, in the present invention, the use of a glycerol ester and a sugar ester is not essential. Specific examples of the constituents include trialkanoyl glycerol, dialkanoyl glycerol, monoalkanoyl glycerol, a sucrose ester, and the like. Specifically, it is possible to use trioleoyl glycerol (glyceryl trioleate), dioleoyl glycerol (glyceryl dioleate), monooleoyl glycerol, or a mixture of these.

When a glycerol ester or a sugar ester is used in the present invention, the amount of the glycerol ester or sugar ester is preferably from 0.01 mol % to 40 mol %, more preferably from 1 mol % to 35 mol %, and even more preferably from 5 mol % to 30 mol % of a total amount of lipid (including a glycerol ester, a sugar ester, and a sterol) constituting the lipid particle.

(2) Lipid Particle (a) Structure of Lipid Particle

In the present invention, the lipid particle refers to a particle constituted a with lipid and is not particularly limited. The lipid particle of the present invention includes a liposome which is a closed vesicle constituted with a lipid bilayer membrane and having a lamellar structure. As the liposome, structures such as a multilamellar liposome (MLV), a small unilamellar liposome (SUV), and a giant unilamellar liposome are known, but the liposome is not particularly limited. The lipid particle of the present invention also includes a particle which has a structure in which the constituents also fill the inside of the particles, instead of the lipid bilayer membrane structure (lamellar structure) that the aforementioned liposome has. As the lipid particle, a non-liposomal particle is preferable, and particularly, a particle which has a structure in which the constituents also fill the inside of the particles, instead of the lipid bilayer membrane structure (lamellar structure) is preferable.

Whether the lipid particle has been formed can be confirmed by structural analysis or the like conducted by electron microscopy or X-ray. For example, by a method using cryogenic transmission electron microscopy (CryoTEM method), the lipid particle is found not to have a structure having the lipid bilayer membrane structure (lamellar structure) or an internal water layer unlike a liposome or the lipid bilayer structure (lamellar structure) or an internal water layer unlike a liposome, and found to have a core with high electron density inside the particle. As a result, it is possible to confirm that the lipid particle has a structure filled with the constituents including lipid. Whether or not the lipid particle has the lipid bilayer membrane structure (lamellar structure) can also be confirmed by measurement using small-angle X-ray scattering (SAXS).

(b) Particle Size of Lipid Particle

The particle size of the lipid particle of the present invention is not particularly limited. However, the particle size is preferably 20 nm to 600 nm, more preferably 30 nm to 590 nm, and even more preferably 40 nm to 560 nm. The particle size of the lipid particle can be measured by a general method (for example, a dynamic light scattering method or the like).

(3) Manufacture of Lipid Particle

The lipid particle of the present invention can be manufactured by a step of manufacturing a dispersion consisting of a nucleic acid and a lipid by mixing an organic solvent solution, which contains a phospholipid having one or more amino groups and one or more nitrogen-containing heterocyclic groups, a neutral lipid not containing a nitrogen-containing heterocyclic group, and a sterol, with a solution containing a nucleic acid, and a step of removing the organic solvent from the dispersion. More specifically, for example, the lipid particle can be manufactured by the following method. First, an aqueous solution containing a nucleic acid or a buffer and a lipid solution obtained by dissolving lipid (lipid containing one or more amino groups and one or more nitrogen-containing heterocyclic groups, a neutral lipid not containing a nitrogen-containing heterocyclic group, a sterol, PEG lipid if necessary, and other constituents such as a lipid having an antibody or a ligand if necessary) in an organic solvent are prepared. Thereafter, the lipid solution prepared as above is added to the aqueous solution containing a nucleic acid or the buffer prepared as above under stirring, thereby preparing a dispersion consisting of a nucleic acid and a lipid. By removing the organic solvent from the obtained dispersion, an intended dispersion of lipid particles can be prepared. If necessary, the obtained dispersion of lipid particles can be subjected to sizing or concentration.

(a) Preparation of Aqueous Solution Containing Nucleic Acid or Buffer

In the present invention, the pH of the buffer is not particularly limited, and a known buffer with a pH of 2 to pH of 10 can be used. A buffer with a pH of 2.5 to pH of 9 is preferable, and a buffer with a pH of 3 to pH of 8.5 is particularly preferable. Particularly, it is preferable to use a medically acceptable buffer. If necessary, constituents other than the nucleic acid of the lipid particle may be added to the aqueous solution containing a nucleic acid or the buffer. When the constituents other than the nucleic acid are added, it is preferable for the constituents to be water-soluble.

(b) Preparation of Lipid Solution

In the present invention, the organic solvent used for preparing a lipid solution is not particularly limited. However, it is preferable for the organic solvent to be water-soluble, and particularly, an alcohol (for example, ethanol, 1-propanol, 2-propanol, 1-butanol, 2-butanol, 3-methyl-1-butanol, and the like), a ketone (for example, acetone, methyl ethyl ketone, methyl isobutyl ketone, and the like), an ether (for example, tetrahydrofuran), and the like are preferable.

(c) Mixing Aqueous Solution Containing Nucleic Acid or Buffer with Lipid Solution In order to mix the aqueous solution containing a nucleic acid or the buffer with the lipid solution, the lipid solution may be added or added dropwise to the aqueous solution containing a nucleic acid or the buffer under stirring. Moreover, a micromixer and a micro-flow path device may be used to mix the aqueous solution containing a nucleic acid or the buffer with the lipid solution. The mixing temperature is not particularly limited, but is preferably within a range of 0° C. to 80° C., more preferably within a range of 5° C. to 70° C., and particularly preferably within a range of 10° C. to 60° C.

(d) Removing Organic Solvent from Dispersion

For removing the organic solvent from the dispersion obtained by mixing the aqueous solution containing a nucleic acid or the buffer with the lipid solution, for example, various methods utilizing dialysis can be used. For dialysis, general methods using a dialysis membrane can be used. The cut-off molecular weight thereof is not particularly limited, but is preferably from 5,000 to 30,000, and more preferably from 10,000 to 20,000. As a dialysate, water or a buffer with various pH levels can be used. By performing dialysis by using an intended dialysate, the dispersion can be substituted with a solution that meets the intended purpose.

(e) Sizing

If necessary, the obtained lipid particle can be subjected to sizing. For the sizing, the particle suspension is treated with ultrasonic waves in a tank or by a probe, whereby the particle size can be reduced.

(f) Concentration

The obtained lipid particle dispersion can be concentrated. For the concentration, various known methods can be used. For example, it is possible to use a method of concentrating the dispersion by using an ultrafiltration membrane.

(4) Utilization of Lipid Particle

For example, the lipid particle of the present invention is transferred into a cell in vitro, and in this manner, a nucleic acid (gene) can be transferred into the cell.

Moreover, when a nucleic acid used for a medical purpose is used as the nucleic acid contained in the lipid particle of the present invention, the lipid particle of the present invention can be administered into the body as a nucleic acid medicine.

When being used as a nucleic acid medicine, the lipid particle of the present invention can be administered into the body singly or by being mixed with a pharmaceutically acceptable dosing vehicle (for example, physiological saline or a phosphate buffer). The concentration of the lipid particle in the mixture consisting of the pharmaceutically acceptable carrier and the lipid particle is not particularly limited, but the concentration generally can be controlled to be 0.05% by mass to 90% by mass. Moreover, other pharmaceutically acceptable additives such as a pH regulating buffer and an osmotic pressure regulator may be added to the nucleic acid medicine containing the lipid particle of the present invention.

When being administered in vivo, the nucleic acid medicine containing the lipid particle of the present invention can be administered through any route by any method without particular limitation. The medicine may be administered by oral administration or parenteral administration (for example, intraarticular administration, intravenous administration, intraperitoneal administration, subcutaneous administration, intramuscular administration, or the like). The nucleic acid medicine containing the lipid particle of the present invention can also be administered by being directly injected into an affected site.

The preparation suitable for parenteral administration can contain an appropriate additives such as an antioxidant, a buffer, a bacteriostatic agent, an isotonic sterile injection, a suspending agent, a solubilizing agent, a thickening agent, a stabilizing agent, and a preservative. When being orally administered, the lipid particle of the present invention can be used in the form of a tablet, a trochiscus, a capsule, a pill, a suspension, or a syrup by being combined with an appropriate excipient. However, the form of the lipid particle is not limited to these.

The dose of the lipid particle can be appropriately determined according to the ratio between the nucleic acid as a medicine and total lipid, the type of nucleic acid to be used, the disease to be treated, the age, weight, condition, and the like of a patient, and the like. For example, the lipid particle can be administered in an amount of about 0.01 mg to 300 mg per 1 kg of body weight in a single dose.

(5) Nucleic Acid Transfer Carrier and Compound for Manufacturing Nucleic Acid Transfer Carrier According to the aforementioned lipid particle which contains, as constituents, a phospholipid having one or more amino groups and one or more nitrogen-containing heterocyclic groups, a neutral lipid not containing a nitrogen-containing heterocyclic group, a sterol, and a nucleic acid, it is possible to make the nucleic acid effectively perform its original function in a target cell. This means that a compound, which consists of a combination of phospholipids having one or more amino groups and one or more nitrogen-containing heterocyclic groups, a neutral lipid not containing a nitrogen-containing heterocyclic group, and a sterol, is useful as a nucleic acid transfer carrier. That is, according to the present invention, there is provided a nucleic acid transfer carrier containing a phospholipid having one or more amino groups and one or more nitrogen-containing heterocyclic groups, a neutral lipid not containing a nitrogen-containing heterocyclic group, and a sterol. Moreover, according to the present invention, there is provided a compound for manufacturing a nucleic acid transfer carrier that contains, as constituents, a phospholipid having one or more amino groups and one or more nitrogen-containing heterocyclic groups, a neutral lipid not containing a nitrogen-containing heterocyclic group, a sterol, and an organic solvent. Specific examples, preferable examples, and the like of the phospholipid having one or more amino groups and one or more nitrogen-containing heterocyclic groups, a neutral lipid not containing a nitrogen-containing heterocyclic group, and a sterol are as described above in the present specification. Further, specific examples of the organic solvent used in the compound for manufacturing a nucleic acid transfer carrier are as described above in the section of "(b) Preparation of Lipid Solution" of "(3) Manufacture of Lipid Particle" in the present specification.

The nucleic acid transfer carrier of the present invention can transfer a nucleic acid into a cell by means of, for example, transfecting the cell with a lipid particle, which has been mixed with the nucleic acid, in vitro. That is, the nucleic acid transfer carrier of the present invention is useful as a gene transfer reagent. Moreover, as described above, the nucleic acid transfer carrier of the present invention is also useful as a nucleic acid transfer carrier in a nucleic acid medicine.

EXAMPLES

Hereinafter, the present invention will be described in more detail based on examples, but the scope of the present invention is not limited to the following examples.

In the present invention, COATSOME ME8181 (registered trademark) manufactured by NOF CORPORATION was used as 1,2-dioleoyl-s,n-glycero-3-phosphoethanolamine (DOPE); COATSOME ME6060 (registered trademark) manufactured by NOF CORPORATION was used as 1,2-dipalmitoyl-s,n-glycero-3-phosphoethanolamine (DPPE); and COATSOME ME8282 (registered trademark) manufactured by NOF CORPORATION was used as 1,2-dilinoleoyl-s,n-glycero-3-phosphoethanolamine (DLoPE). Moreover, as 1,2-diphytanoyl-s,n-glycero-3-phosphoethanolamine (D(Phy)PE), a product manufactured by Avanti Polar Lipids, Inc. was used, and as cholesterol, a product manufactured by Wako Pure Chemical Industries, Ltd. was used.

Synthesis Example 1

Synthesis of Compound 1-5

692 mg of DPPE, 680 mg of Boc-His(Boc)-OSu (manufactured by Bachem), and 303 mg of triethylamine (manufactured by Wako Pure Chemical Industries, Ltd.) were dissolved in 20 mL of chloroform. The resultant was stirred for 6 hours, and then concentrated and dried under reduced pressure. Water was added to the residues to make a suspension, and then the suspension was subjected to dialysis and freeze-drying, thereby obtaining 676 mg of white powder. The obtained white powder was dissolved in 30 mL of dioxane, 30 mL of a dioxane solution containing 4M hydrochloric acid was added thereto, and the resultant was stirred for 15 minutes. Thereafter, the resultant was heated to 60° C. and cooled. The thus obtained white solids were collected by filtration, thereby obtaining 631 mg of a compound 1-5 (hydrochloride).

FAB-MS 828.6 (M+H)+

Synthesis Example 2

Synthesis of Compound 1-7

1.49 g of DOPE, 1.36 g of Boc-His(Boc)-OSu (manufactured by Bachem), and 0.61 g of triethylamine (manufactured by Wako Pure Chemical Industries, Ltd.) were dissolved in 40 mL of chloroform, and the solution was stirred for 24 hours. After being washed with a 0% aqueous citric acid solution, the reaction solution was washed with a saturated aqueous carbonic acid solution and dried over anhydrous sodium sulfate. The reaction solution was concentrated and dried under reduced pressure, and the thus obtained colorless syrup was dissolved in 30 mL of dioxane. Subsequently, 30 mL of a dioxane solution containing 4M hydrochloric acid was added thereto, and the reaction solution was stirred for 1 hour. Thereafter, the reaction solution was concentrated and dried under reduced pressure, and water was added to the thus obtained residues to form a suspension. The suspension was then subjected to dialysis and freeze-drying, thereby obtaining 0.96 g of a compound 1-7 (hydrochloride) in the form of white powder.

FAB-MS 881.4 (M+H)+

Synthesis Example 3

Synthesis of Compound 4-5

1 mg of SUNBRIGHT DSPE-020GS (manufactured by NOF CORPORATION, registered trademark) and 1 mg of c(RGDfK) (manufactured by Bachem) were dissolved in 0.5 mL of PBS (pH 7.4), and the solution was stirred for two days. The reaction solution was subjected to dialysis and freeze drying, thereby obtaining about 1 mg of a compound 4-5 in the form of white powder. By TOF-MS, it was confirmed that the molecular weight thereof increased by 467, which showed that an intended compound was formed.

Synthesis Example 4

Synthesis of Compound 4-6

A solution obtained by dissolving 25 mg of SUNBRIGHT DSPE-020MA (manufactured by NOF CORPORATION, registered trademark) in 1 mL of a 20 mM tris-HCl buffer (pH 7.5) and dissolving 5 mg of c(RGDfC) (manufactured by Bachem) in 1 mL of a 20 mM tris-HCl buffer (pH 7.5) was stirred for 24 hours at room temperature. The reaction solution was subjected to dialysis and freeze-drying, thereby obtaining 22 mg of a compound 4-6 in the form of white powder. By TOF-MS, it was confirmed that the molecular weight thereof increased by 556, which showed that an intended compound was formed.

Example 1

Preparation of Lipid Particle (Method A)

1.27 mL of a lipid alcohol solution, which was prepared such that a total lipid concentration became 65 mM in terms of an average molecular weight, was added under stirring to 0.1 mL of a 100 mM histidine buffer (pH 7) in which 0.5 mg of siRNA had dissolved, and then 1.65 mL of sterile water was added thereto. Subsequently, a dispersion consisting of siRNA and the lipid that was obtained in the above-described manner was dialyzed with a 100 mM histidine buffer (pH 7) by using Slide-A-Lyzer G2 (registered trademark), thereby obtaining an intended lipid particle dispersion.

As the siRNA, RNA having the following sequence was used. Moreover, as the lipid alcohol solution, A-1 to A-11 having the composition shown in the following Table 1 were used.

```
siRNA 1
                                          (SEQ ID NO: 1)
5'-GUUCAGACCACUUCAGCUUTT-3' (sense)

(SEQ ID NO: 2)
5'-AAGCUGAAGUGGUCUGAACTT-3' (antisense)
```

Example 2

Preparation of Lipid Particle (Method B)

1.27 mL of a lipid alcohol solution, which was prepared such that a total lipid concentration became 65 mM in terms of an average molecular weight, was added under stirring to 0.1 mL of sterile water in which 0.5 mg of siRNA had dissolved, and then 1.65 mL of sterile water was added thereto. Subsequently, a dispersion consisting of siRNA and the lipid that was obtained in the above-described manner was dialyzed with water by using Slide-A-Lyzer G2 (registered trademark), thereby obtaining an intended lipid particle dispersion.

As the siRNA, RNA having the following sequence was used. Moreover, as the lipid alcohol solution, B-1 to B-4 having the composition shown in the following Table 2 were used.

```
siRNA 1
                                          (SEQ ID NO: 1)
5'-GUUCAGACCACUUCAGCUUTT-3' (sense)

(SEQ ID NO: 2)
5'-AAGCUGAAGUGGUCUGAACTT-3' (antisense)
```

TABLE 1

| Sample No. | Lipid Composition | siRNA |
| --- | --- | --- |
| A-1 | Compound 1-7/DOPE/cholesterol/SUNBRIGHT DSPE-020CN(NOF, registered trademark)/Compound 4-5 = 9.9/49.7/39.8/0.1/0.5 | siRNA-1 |
| A-2 | Compound 1-7/DOPE/cholesterol/SUNBRIGHT DSPE-020CN(NOF, registered trademark)/Compound 4-5 = 9.9/49.5/39.6/0.1/1 | siRNA-1 |
| A-3 | Compound 1-7/DOPE/DPPE/cholesterol/SUNBRIGHT DSPE-020CN(NOF, registered trademark)/Compound 4-5 = 9.9/39.6/9.9/39.6/0.1/1 | siRNA-1 |
| A-4 | Compound 1-7/DOPE/D(phy)PE/cholesterol/SUNBRIGHT DSPE-020CN(NOF, registered trademark)/Compound 4-5 = 9.9/39.8/9.9/39.6/0.1/1 | siRNA-1 |
| A-5 | Compound 1-7/DOPE/DLoPE/cholesterol/SUNBRIGHT DSPE-020CN(NOF, registered trademark)/Compound 4-5 = 9.9/39.8/9.9/39.6/0.1/1 | siRNA-1 |
| A-6 | Compound 1-7/DOPE/cholesterol/SUNBRIGHT DSPE-020CN(NOF, registered trademark)/Compound 4-5 = 19.9/59.6/19.9/0.1/0.5 | siRNA-1 |
| A-7 | Compound 1-7/DOPE/cholesterol/SUNBRIGHT DSPE-020CN(NOF, registered trademark)/Compound 4-1 = 9.9/49.5/39.6/0.1/1 | siRNA-1 |
| A-8 | Compound 1-7/DOPE/cholesterol/SUNBRIGHT DSPE-020CN(NOF, registered trademark)/Compound 4-5 = 49.7/9.9/39.8/0.1/1 | siRNA-1 |
| A-9 | Compound 1-7/DOPE/cholesterol/SUNBRIGHT DSPE-020CN(NOF, registered trademark)/Compound 4-5 = 29.7/29.7/39.6/0.1/1 | siRNA-1 |
| A-10 | Compound 1-7/DOPE/cholesterol/SUNBRIGHT DSPE-020CN(NOF, registered trademark)/Compound 4-5 = 49.5/29.7/19.8/0.1/1 | siRNA-1 |
| A-11 | Compound 1-5/DOPE/cholesterol/Compound 4-6 = 32/32/25/1 | siRNA-1 |

TABLE 2

| Sample No. | Lipid composition | siRNA |
|---|---|---|
| B-1 | Compound 1-7/DOPE/cholesterol/Compound 4-5 = 10/49/40/1 | siRNA-1 |
| B-2 | Compound 1-7/DOPE/cholesterol/Compound 4-5 = 20/49/40/1 | siRNA-1 |
| B-3 | Compound 1-7/DOPE/cholesterol/Compound 4-5 = 29.7/29.7/39.6/1 | siRNA-1 |
| B-4 | Compound 1-5/DOPE/cholesterol/SUNBRIGHT DSPE-020CN (NOF, registered trademark)/Compound 4-5/egg yolk ceramide = 5/45/39/0.1/1/10 | siRNA-1 |

Example 3

Preparation of Lipid Particle (Method B)

A lipid particle (sample No. C-1) which contained, as a constituent, NIKKOL DGO-80 (manufactured by Nikko Chemicals Co., Ltd., registered trademark) as a glycerol oleic acid ester and a lipid particle (sample No. C-2) which contained, as a constituent, O-170 (manufactured by Mitsubishi-Kagaku Foods Corporation, registered trademark) as a sucrose oleic acid ester were prepared by the method of Example 2.

TABLE 3

| Sample No. | Lipid composition | siRNA |
|---|---|---|
| C-1 | Compound 1-7/DOPE/NIKKOL DGO-80 (Nikko Chemicals Co., Ltd., registered trademark)/Compound 4-5 = 19.9/49.8/10/19.9/0.4 | siRNA-1 |
| C-2 | Compound 1-7/DOPE/sucrose oleic acid ester O-170 (Mitsubishi-Kagaku Foods Corporation, registered trademark)/Compound 4-5 = 10/49.8/10/29.8/0.4 | siRNA-1 |

Example 4

Confirmation of Lipid Particle by Using Cryogenic Transmission Electron Microscopy (CryoTEM Method)

The lipid particles (sample No. A-2 and sample No. B-4) of the present invention were observed by cryogenic transmission electron microscopy. The cryogenic transmission electron microscopy is described in International Journal of Pharmaceutics, 417 (2011), 120-137. By the observation, it was found that the lipid particles of sample No. A-2 and sample No. B-4 did not have a lipid bilayer membrane structure (lamellar structure) or an internal water layer and had a core with high electron density inside the particle. As a result, the particles was confirmed to be lipid particles filled with constituents including a lipid.

Example 5

Particle Size Measurement

The particle size of the lipid particle was measured using a zeta-potential particle size analyzing system manufactured by OTSUKA ELECTRONICS CO., LTD., by means of diluting the lipid particle dispersion with water or the used buffer within a 10-fold to 50-fold range.

Example 6

Evaluation of Target mRNA Production Inhibition Rate in Cell (1) Transfection of Lipid Particle into Cell A 24-well plate in which $0.9 \times 10^3$ TOV112D cells (cell strain of human ovarian cancer) were seeded was prepared. After 24 hours, the medium thereof was replaced with 200 μL of Opti-MEM (registered trademark). Thereafter, 100 μL of a lipid particle dispersion, which was diluted with Opti-MEM (registered trademark) such that the concentration thereof became three times higher than the treatment concentration, was added to the 24-well plate (total solution amount of 300 μl). Subsequently, the cells were cultured for 24 hours to 48 hours in a 5% $CO_2$ incubator. Moreover, as a positive control, lipofectamine 2000 (registered trademark) was used instead of the lipid particle dispersion, and the same examination as above was conducted.

(2) Extraction of Total RNA

After culturing, total RNA was extracted from the cells by using the RNeasy Mini Kit (manufactured by QIAGEN, registered trademark). An absorbance showing the concentration of the extracted total RNA was measured, and then the total RNA was diluted with RNase-free water such that the RNA concentration became 5 ng/μL.

(3) Quantitative PCR

A reverse transcription reaction and PCR were performed using the QUANTIFAST PROBE RTPCR KIT (manufactured by QIAGEN, registered trademark). Quantitative PCR was performed using the TaqMan Gene expression assay (manufactured by Applied Biosystems, Inc., registered trademark) as a primer/probe for the used siRNA gene and Mx3000P (manufactured by Agilent Technologies, registered trademark). The PCR was performed under conditions of 50° C. and 30 minutes, 95° C. and 15 minutes, 94° C. and 15 seconds, and 60° C. and 30 seconds (40 cycles). As an internal standard, TaqMan Encogeneous Control Human ACTB (Applied Biosystems, Inc., registered trademark) was used. The obtained data was used to calculate an mRNA production inhibition rate by a ΔΔCT method, by means of determining the amount of mRNA relative to the mRNA of untransfected cells.

Table 4 shows the mRNA production inhibition rate obtained when the samples of No. A-1 to No. A-11 shown in Table 1 and lipofectamine 2000 (registered trademark) were used.

Table 5 shows the mRNA production inhibition rate obtained when the samples of No. B-1 to No. B-4 shown in Table 2 and lipofectamine 2000 (registered trademark) were used.

Table 6 shows the mRNA production inhibition rate obtained when the samples of No. C-1 and No. C-2 shown in Table 3 and lipofectamine 2000 (registered trademark) were used.

TABLE 4 mRNA Production Inhibition Rate of Lipid Particle Carrier of the Present Invention

| Sample No. | SiRNA concentration (nM) | mRNA production inhibition rate (%) | Particle size (nm) | siRNA/Lipid (wt/wt) |
|---|---|---|---|---|
| A-1 | 12 | 79 | 312 | 0.01 |
|  | 40 | 87 |  |  |
|  | 80 | 87 |  |  |
| A-2 | 9 | 68 | 247 | 0.01 |
|  | 30 | 68 |  |  |
|  | 61 | 80 |  |  |
| A-3 | 13 | 51 | 288 | 0.01 |
|  | 43 | 56 |  |  |
|  | 86 | 62 |  |  |
| A-4 | 13 | 42 | 205 | 0.01 |
|  | 42 | 56 |  |  |
|  | 85 | 68 |  |  |
| A-5 | 1 | 70 | 322 | 0.01 |
|  | 2 | 55 |  |  |
|  | 5 | 65 |  |  |
| A-6 | 21 | 65 | 340 | 0.01 |
|  | 71 | 83 |  |  |
|  | 141 | 88 |  |  |
| A-7 | 100 | 80 | 451 | 0.07 |
|  | 335 | 90 |  |  |
|  | 669 | 89 |  |  |
| A-8 | 14 | 32 | 141 | 0.02 |
|  | 45 | 44 |  |  |
|  | 90 | 43 |  |  |
| A-9 | 17 | 27 | 168 | 0.01 |
|  | 55 | 35 |  |  |
|  | 110 | 54 |  |  |
| A-10 | 18 | 46 | 138 | 0.01 |
|  | 60 | 70 |  |  |
|  | 120 | 57 |  |  |
| A-11 | 30 | 23 | 581 | 0.02 |
|  | 100 | 43 |  |  |
|  | 200 | 46 |  |  |
| lipofectamine 2000 | 1 | 34 |  |  |
|  | 10 | 44 |  |  |
|  | 30 | 79 |  |  |
|  | 60 | 82 |  |  |

TABLE 5 mRNA Production Inhibition Rate of Lipid Particle Carrier of the Present Invention

| Sample No. | siRNA concentration (nM) | mRNA production inhibition rate (%) | Particle size (nm) | siRNA/Lipid (wt/wt) |
|---|---|---|---|---|
| B-1 | 25 | 72 | 197 | 0.02 |
|  | 83 | 87 |  |  |
|  | 165 | 89 |  |  |
| B-2 | 6 | 81 | 226 | 0.01 |
|  | 19 | 88 |  |  |
|  | 38 | 89 |  |  |
| B-3 | 46 | 57 | 178 | 0.04 |
|  | 155 | 65 |  |  |
|  | 309 | 79 |  |  |
| B-4 | 30 | 37 | 235 | 0.04 |
|  | 100 | 75 |  |  |
|  | 200 | 83 |  |  |
| lipofectamine 2000 | 1 | 34 |  |  |
|  | 10 | 44 |  |  |
|  | 30 | 79 |  |  |
|  | 60 | 82 |  |  |

TABLE 6 mRNA Production Inhibition Rate of Lipid Particle Carrier of the Present Invention

| Sample No. | siRNA concentration (nM) | mRNA production inhibition rate (%) | Particle size (nm) | siRNA/Lipid (wt/wt) |
|---|---|---|---|---|
| C-1 | 30 | 54 | 149 | 0.02 |
|  | 100 | 70 |  |  |
|  | 200 | 84 |  |  |
| C-2 | 85 | 52 | 669 | 0.04 |
|  | 285 | 84 |  |  |
|  | 569 | 78 |  |  |
| lipofectamine 2000 | 1 | 34 |  |  |
|  | 10 | 44 |  |  |
|  | 30 | 79 |  |  |
|  | 60 | 82 |  |  |

Comparative Example 1

Preparation of Lipid Particle as Comparative Example (Method B)

A lipid particle as a comparative example having the lipid composition shown in Table 7 was prepared in the same manner as described in Example 2. The samples of No. D-1 and No. D-2 are lipid particles not containing "phospholipid having one or more amino groups and one or more nitrogen-containing heterocyclic substituents".

TABLE 7

| Sample No. | Lipid composition | siRNA |
|---|---|---|
| D-1 | DOPE/SUNBRIGHT DSPE-020CN (NOF, registered trademark)/Compound 4-5 = 99/0.1/1 | siRNA-1 |
| D-2 | DOPE/cholesterol/Compound 4-5 = 60/40/0.1 | siRNA-1 |

Comparative Example 2

Evaluation of Target mRNA Production Inhibition Rate in Cell

As a comparative example, a target mRNA production inhibition rate in a cell of the lipid particle not containing "phospholipid having one or more amino groups and one or more nitrogen-containing heterocyclic substituents" was evaluated in the same manner as described in Example 6. The results are shown in Table 8.

The lipid particle not containing "phospholipid having one or more amino groups and one or more nitrogen-containing heterocyclic substituents" did not exhibit a siRNA concentration-dependent target mRNA production inhibitory action.

TABLE 8 mRNA Production Inhibition Rate of Lipid Particle Carrier as Comparative Example

| Sample No. | siRNA concentration (nM) | mRNA production inhibition rate (%) | Particle size (nm) | siRNA/Lipid (wt/wt) |
|---|---|---|---|---|
| D-1 | 30 | −14 | Coarsening | 0.03 |
|  | 100 | 0 |  |  |
|  | 200 | 4 |  |  |
| D-2 | 17 | 39 | 364 | 0.01 |
|  | 57 | 26 |  |  |
|  | 114 | 24 |  |  |
| lipofectamine 2000 | 1 | 34 |  |  |
|  | 10 | 44 |  |  |
|  | 30 | 79 |  |  |
|  | 60 | 82 |  |  |

From the above results, it was found that according to the lipid particle of the present invention that contains "phospholipid having one or more amino groups and one or more nitrogen-containing heterocyclic substituents", a nucleic acid molecule can be stably held outside a cell (in blood); the particle can escape from the endosome and can rapidly release the nucleic acid in the cytoplasm; and it is possible to make the nucleic acid perform its original function in a target cell.

Example 7

Cytotoxicity of Lipid Particle

On the day before treatment, $1.0 \times 10^4$ Chinese hamster ovarian (CHO) cells were seeded in a 96-well plate (medium amount of 100 μl/well). After the cells were cultured for 12 hours or longer in a 5% $CO_2$ incubator, the medium was removed by an amount of 50 μl. The lipid particles were diluted with OPTI-MEM such that the final concentration thereof became 2 times higher than that of the final concentration. After the diluted solution was added to the plate in an amount of 50 μl/well, the cells were cultured again for 24 hours in the 5% $CO_2$ incubator.

After the 24 hours of culturing, viability and cytotoxicity of the cells were evaluated by the MultiTox-Glo Multiplex Cytotoxicity Assay (manufactured by Promega Corporation). The living cell-derived protease activity was measured by λex/λem=405 nm/488 nm by using Infinite s200 (manufactured by Tecan Trading AG), and the dead cell-derived protease activity was measured using Envision (manufactured by PerkinElmer Inc.). IC50 or EC50 was calculated using GraphPad Prism 5.0.

By using a lipid particle composed of the compound 1-7/DOPE/cholesterol/compound 4-5 (20/40/40/0.1) and prepared according to Example 2, cytotoxicity was evaluated. The cytotoxicity evaluation results are shown in Table 9.

TABLE 9

Cytotoxicity Evaluation Results

| Sample | Cytotoxicity EC50 | Cell viability IC50 |
|---|---|---|
| Lipofectamine 2000 | 16.3 nM | 9.6 nM |
| Lipid particle of the present invention | >500 nM | >500 nM |

From Table 9, it was found that cytotoxicity of the carrier of the present invention is lower than that of lipofectamine 2000 (registered trademark) as a gene transfer reagent.

What is claimed is:

1. A lipid particle comprising, as constituents:
   a phospholipid having one or more amino groups and one or more nitrogen-containing heterocyclic groups;
   a neutral lipid not containing a nitrogen-containing heterocyclic group;
   a sterol; and
   a nucleic acid,
   wherein the phospholipid having one or more amino groups and one or more nitrogen-containing heterocyclic groups is a lipid represented by the following Formula (I) or a salt thereof, Formula (I)

[Chem. 1]

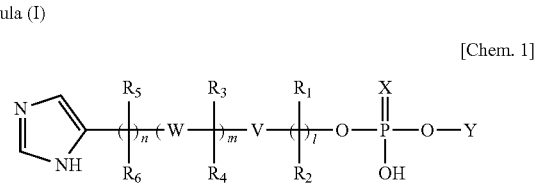

in Formula (I), X represents an oxygen atom or a sulfur atom; Y represents a hydrophobic group; each of W and V independently represents a single bond, —O—, —NH—, —CO—, or a linking group as a combination of these; each of $R_1$ and $R_2$ independently represents a hydrogen atom or an alkoxycarbonyl group having 1 to 4 carbon atoms; each of $R_3$ and $R_4$ independently represents a hydrogen atom, an alkyl group having 1 to 4 carbon atoms, a hydroxyalkyl group having 1 to 4 carbon atoms, an alkoxycarbonyl group having 1 to 4 carbon atoms, an aminoalkyl group having 1 to 4 carbon atoms, a guanidinoalkyl group having 1 to 4 carbon atoms, or an imidazolylalkyl group having 4 to 7 carbon atoms; each of $R_5$ and $R_6$ independently represents a hydrogen atom, an amino group, or an alkoxycarbonyl group having 1 to 4 carbon atoms; when n is 1, at least one of $R_5$ and $R_6$ represents an amino group; when n is an integer from 2 to 4, at least one of the plural $R_5$s and plural $R_6$s contained in Formula (I) represents an amino group; l represents an integer from 2 to 4; m represents an integer from 0 to 4; and n represents an integer from 1 to 4.

2. The lipid particle according to claim 1,
   wherein the phospholipid having one or more amino groups and one or more nitrogen-containing heterocyclic groups is a phospholipid having one or more amino groups and one or more imidazolyl groups.

3. The lipid particle according to claim 1,
   wherein the phospholipid having one or more amino groups and one or more nitrogen-containing heterocyclic groups has a structure in which a carboxyl group of histidine is bonded to an amino group of phospholipid having the amino group.

4. The lipid particle according to claim 2, wherein the phospholipid having one or more amino groups and one or more nitrogen-containing heterocyclic groups has a structure in which a carboxyl group of histidine is bonded to an amino group of phospholipid having the amino group.

5. The lipid particle according to claim 1, wherein the phospholipid having one or more amino groups and one or more nitrogen-containing heterocyclic groups is a lipid represented by the following Formula (II) or Formula (III) or a salt thereof, Formula (II)

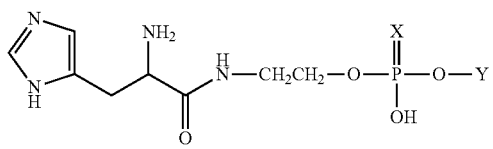

in Formula (II), X represents an oxygen atom or a sulfur atom, and Y represents a hydrophobic group, Formula (III)

[Chem. 3]

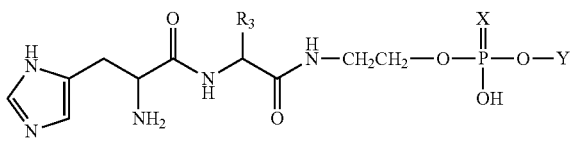

in Formula (III), $R_3$ represents a hydroxyalkyl group having 1 to 4 carbon atoms or an imidazolylalkyl group having 4 to 7 carbon atoms; X represents an oxygen atom or a sulfur atom; and Y represents a hydrophobic group.

6. The lipid particle according to claim 1, wherein the neutral lipid not containing a nitrogen-containing heterocyclic group is a phosphatidylethanolamine.

7. The lipid particle according to claim 1, wherein the neutral lipid not containing a nitrogen-containing heterocyclic group is a phosphatidylethanolamine having a phase transition point of equal to or lower than 0° C.

8. The lipid particle according to claim 1, wherein the sterol is cholesterol.

9. The lipid particle according to claim 1, further comprising polyethylene glycol-containing lipid.

10. The lipid particle according to claim 1, further comprising a lipid having an antibody or a ligand.

11. The lipid particle according to claim 10, wherein the lipid having an antibody or a ligand is a lipid having a polyethylene glycol chain.

12. The lipid particle according to claim 1, wherein the nucleic acid is miRNA, aiRNA, or siRNA.

13. A method for manufacturing the lipid particle according to claim 1, comprising:
a step of manufacturing a dispersion consisting of a nucleic acid and a lipid by mixing an organic solvent solution, which contains a phospholipid having one or more amino groups and one or more nitrogen-containing heterocyclic groups, a neutral lipid not containing a nitrogen-containing heterocyclic group, and a sterol, with a solution containing a nucleic acid; and
a step of removing the organic solvent from the dispersion,
wherein the phospholipid having one or more amino groups and one or more nitrogen-containing heterocyclic groups is a lipid represented by the following Formula (I) or a salt thereof, Formula (I)

[Chem. 1]

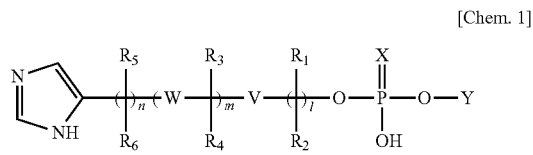

in Formula (I), X represents an oxygen atom or a sulfur atom; Y represents a hydrophobic group; each of W and V independently represents a single bond, —O—, —NH—, —CO—, or a linking group as a combination of these; each of $R_1$ and $R_2$ independently represents a hydrogen atom or an alkoxycarbonyl group having 1 to 4 carbon atoms; each of $R_3$ and $R_4$ independently represents a hydrogen atom, an alkyl group having 1 to 4 carbon atoms, a hydroxyalkyl group having 1 to 4 carbon atoms, an alkoxycarbonyl group having 1 to 4 carbon atoms, an aminoalkyl group having 1 to 4 carbon atoms, a guanidinoalkyl group having 1 to 4 carbon atoms, or an imidazolylalkyl group having 4 to 7 carbon atoms; each of $R_5$ and $R_6$ independently represents a hydrogen atom, an amino group, or an alkoxycarbonyl group having 1 to 4 carbon atoms; when n is 1, at least one of $R_5$ and $R_6$ represents an amino group; when n is an integer from 2 to 4, at least one of the plural $R_5$s and plural $R_6$s contained in Formula (I) represents an amino group; l represents an integer from 2 to 4; m represents an integer from 0 to 4; and n represents an integer from 1 to 4.

14. An intracellular gene transfer method comprising a step of transferring the lipid particle according to claim 1 into a cell in vitro.

15. An intracellular gene transfer method comprising a step of transferring the lipid particle according to claim 2 into a cell in vitro.

16. The lipid particle according to claim 1, wherein Y represents a hydrophobic group selected from the group consisting of an alkyl group having 8 to 24 carbon atoms, an acyl group having 8 to 22 carbon atoms, a 1,2-dialkyloxypropyl group having 16 to 54 carbon atoms, a 1,3-dialkyloxypropyl group having 16 to 54 carbon atoms, a 1,2-diacyloxypropyl group having 16 to 54 carbon atoms, and a 1,3-diacyloxypropyl group having 16 to 54 carbon atoms.

* * * * *